(12) United States Patent
Szilagyi (10) Patent No.: US 6,368,815 B1
(45) Date of Patent: Apr. 9, 2002

(54) SCREENING OF MOLECULES THAT INHIBIT HUMAN PHOSPHODIESTERASE 4A PRODUCED BY NON-RECOMBINANT CELL LINES

(75) Inventor: Corinne Szilagyi, Vitry-sur-Seine (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/528,806

(22) Filed: Mar. 20, 2000

Related U.S. Application Data
(60) Provisional application No. 60/126,669, filed on Mar. 29, 1999.

(51) Int. Cl.[7] ............................. C12Q 1/44; C12N 9/16; C12P 19/24
(52) U.S. Cl. ........................ 435/19; 435/196; 424/94.6
(58) Field of Search ................... 435/19, 196; 424/94.6

(56) References Cited

U.S. PATENT DOCUMENTS

| | | | |
|---|---|---|---|
| 5,922,557 A | * 7/1999 | Pon | 435/21 |
| 5,935,977 A | * 8/1999 | Yamazaki et al. | 514/348 |
| 5,990,103 A | * 11/1999 | Schonharting et al. | 514/211 |

OTHER PUBLICATIONS

Chomczynski, P., et al., Anal. Biochem., 'Single–Step Method of RNA Isolation by Acid Guanidinium Tiocyanate–Phenol–Chloroform Extraction', 1987, vol. 162, pp. 156–159.

Livi, G.P., et al., Molec. Cell Biol., 'Cloning and Expression of cDNA for a Human Low–KM, Rolipram–Sensitive Cyclic AMP Phosphodiesterase', 1990, vol. 10, pp. 2678–2686.

Smith, B.J., et al., Anal. Biochem., 'A Phosphodiesterase Assay Using Alumina Microcolumns', 1993, vol. 214, pp. 355–357.

\* cited by examiner

*Primary Examiner*—David M. Naff
*Assistant Examiner*—Mike Meller
(74) *Attorney, Agent, or Firm*—Charles W. Ashbrook; Mehdi Ganjeizadeh (57) ABSTRACT

An assay for the screening of a candiadte molecule that inhibits the expression or the activity of a human phosphodiesterase 4A (PDE4A) is disclosed. The method comprises incubating non-recombinant cells in the presence of a concentration of a phorbol ester sufficient to significantly increase PDE4A production in the cells. Next, a candidate molecule is added to the culture medium in which the phorbol ester-treated cells are cultured, then the cells are disrupted and harvested to produce a cell lysate. Finally, the cAMP content in the cell lysate is quantified and then the cAMP content in the cell lysate is compared to the cCAMP content in the cell lysate of the phorbol ester treated cells cultured in the absence of the candidate molecule.

6 Claims, 4 Drawing Sheets

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 1
tcggagctgg cgctcatgta c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
ggcagtgtgc ttgtcacaca t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
agctcatgac ccagataagt g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer
```

```
<400> SEQUENCE: 4
gcagcgtgca ggctgttgtg a                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
cgctcagata gcgactatga a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6
tccgcttgaa cttgttggag g                                              21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 7
ggcctccaac aagtttaaaa                                                20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8
accagacaac tctgctattc t                                              21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      5'-biotin-labelled capture probe

<400> SEQUENCE: 9
agcgccagcg cagagcctac                                                20

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:
      5'-biotin-labelled capture probe

<400> SEQUENCE: 10
tagaccccta acatg                                                     15
```

-continued

```
<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      5'-biotin-labelled capture probe

<400> SEQUENCE: 11
agcagccaag cagggaccc                                                  19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      5'-biotin-labelled capture probe

<400> SEQUENCE: 12
caatgtctca gatcagtgga                                                 20
```

SCREENING OF MOLECULES THAT INHIBIT HUMAN PHOSPHODIESTERASE 4A PRODUCED BY NON-RECOMBINANT CELL LINES

This application claims benefit of 60/126,699 filed Mar. 29, 1999.

FIELD OF THE INVENTION

The invention relates to a method for the screening of a non-recombinant cell line capable, under appropriate conditions, of selectively expressing levels of a target protein, preferably an isoenzyme of PDE4A.

The invention also concerns methods for the screening of a candidate molecule that modulates the expression or the activity of human phosphodiesterase 4A.

BACKGROUND OF THE INVENTION

Cyclic nucleotides are important second messengers that regulate and mediate a number of cellular responses to extra-cellular signals, such as hormones, light and neuro-transmitters.

The cyclic nucleotide phosphodiesterases regulate the cellular concentrations of cyclic nucleotides and thereby play a role in signal transduction. To date, nine different classes of phosphodiesterases have been identified and, among them, phosphodiesterase 4, 7, 8 and 9 have been recognized as cAMP-specific enzymes.

Investigations of recent years revealed that isoenzymes of cyclic-3'-5'-nucleotide phosphodiesterases are critically important components of the cyclic-3',5'-adenosine monophosphate (cAMP) protein kinase A (PKA) signalling pathway.

The experimental data suggest that PDE isoenzymes are important in airway inflammation and that PDE inhibitors exert anti-inflammatory effects by acting on airway epithelial cells.

The cAMP phosphodiesterases are proteins encoded by 4 genes in mammals (PDE 4A, B, C, D) that encode multiple PDE isoforms generated from alternative spliced mRNA transcripts. However, the physiological significance of this diversity of cAMP specific PDE isoforms is not yet known, although it has been shown that the rat PDE4 genes have different patterns of expression in tissues.

PDE4 isoenzymes are likely to be good targets for molecules acting in diseases caused or regulated by cyclic nucleotide-modulated transduction mechanisms. Pharmaceutical interest in this area has been further sparked by the hypothesis that different PDE isoenzymes having distinct sequences at regulatory and catalytic sites could allow the development of selective therapeutic agents that can target a specific cyclic nucleotide pool in a very limited number of cell types. This in turn holds great promise of being able to limit the toxic effects of many of the first generation selective PDE4 inhibitors.

Regulation of PDE4 gene expression appears to be a complex process. In various cell-based differentiation systems it has been demonstrated that elevation of intracellular cAMP levels plays a pivotal promoting role.

In general, PDE4 activity can be short-term or long-term regulated; short-term regulation of PDE4 activity is a cAMP-dependent protein kinase phosphorylation of the isoenzyme triggered by intracellular cAMP-elevating agents or a direct activation of PDE4 by phosphatidic acid Long-term up-regulation is also realized by increased intracellular cAMP concentrations but requires both protein and mRNA synthesis. An interesting feature is that different types of regulation can occur in the same cell-type. For example, cells possess a phospholipid-sensitive form of PDE4 which can be activated by anionic phospholipids.

It has been shown that cAMP-increasing agents increased PDE4 activity in this cell-type by enhancement of the transcription of certain PDE4 subtypes (PDE4A and B).

Consequently, there is a great need for new molecules that selectively modulate the expression or the activity of the human PDE 4A, and particularly molecules that are able to inhibit the expression or the activity of the human PDE4A.

SUMMARY OF THE INVENTION

The invention concerns a method for the screening of a non-recombinant cell line capable, under appropriate conditions, of exhibiting an upregulated expression of a target protein (that is increased production of the target protein), preferably of an isoenzyme of PDE4, naturally expressed in the cell. The method comprises:

providing a non-recombinant cell line;

treating the non-recombinant cell line with a concentration of a phorbol ester, preferably PMA, ranging from 0.1 $\mu$M to 3 $\mu$M, for a period of time ranging from 12 hours to 10 days; preferably from 2 to 7 days, more preferably from 4 to 7 days and measuring the amount of target protein produced by the treated non-recombinant cell line and comparing the measured amount with the amount of protein produced under normal culturing conditions by the non-recombinant cell line prior to phorbol ester treatment.

This screening method of the invention exploits the inventor's findings that a human promyelocytic cell line presents significantly upregulated expression of a specific isoenzyme of phosphodiesterase, namely phosphodiesterase 4A, and a substantially downregulated expression of other PDE4 isoenzymes, preferably unmeasurable levels of all other PDE4 isoenzymes, when treated with a phorbol ester such as PMA.

The present invention also concerns methods for the screening of candidate molecules that modulate the expression or the activity of human phosphodiesterase 4A.

A first screening method of the invention comprises the step of quantifying cAMP content in phorbol ester-treated non-recombinant cells incubated with a candidate molecule to be assayed.

A second screening method of the invention comprises a step wherein an expression analysis of human phosphodiesterase 4A is performed. The candidate molecules selected by the screening methods of the invention are potentially useful as therapeutic molecules for diseases caused or regulated by cyclic nucleotide-modulated transduction mechanisms, airway disorders such as asthma, pulmonary hypertension, COPD (constructive obstructive pulmonary disease), CNS related diseases such as depression and other inflammatory disorders including atopic dermatitis psoriasis, Crohn's disease, ulcerative colitis, acute respiratory distress syndrome and rheumatoid arthritis.

The invention also concerns a method for determining the selectivity of is a candidate molecule for a PDE4 subtype The method comprises:

providing a non-recombinant cell line culture presenting a significantly upregulated expression of PDE4A and a substantially downregulated expression of other PDE4 isoenzymes, preferably unmeasurable levels of all other PDE4 isoenzymes;

adding said candidate compound to said cell line culture; and quantifying the cAMP content in said culture.

BRIEF DESCRIPTION OF THE DRAWINGS

FIG. 2: Comparison of the chromatographic profiles of phosphodiesterase activities in PMA-treated HL60 versus control cells.

2A: Phosphodiesterase 4A activity in HL60 control cells, as revealed by hydrolysis of different cyclic monophosphate nucleotides.

2B: Phosphodiesterase 4A activities in PMA-treated HL60 cells, as revealed by hydrolysis of different monophosphate nucleotides.

FIG. 3. Comparison of the chromatographic profiles of phosphodiesterase activities in PMA-treated HK-293 cells versus control cells.

3A: Phosphodiesterase activities of HK-293 control cells, as revealed by hydrolysis of different cyclic monophosphate nucleotides.

3B: Phosphodiesterase activities in PMA-treated HK-293 cells, as revealed by hydrolysis of different cyclic monophosphate nucleotides.

The figures were obtained using the mean values of 3 experiments. The calculated IC50 for rolipram is 1.85 $\mu$M.

DETAILED DESCRIPTION OF THE INVENTION

The inventors have surprisingly found that a promyelocytic human cell line that normally expresses different phosphodiesterase 4 isoenzymes, such as PDE 4A, PDE 4B and PDE 4D, and mainly the PDE 4B isoenzyme, expresses exclusively the PDE 4A isoenzyme when treated with an appropriate concentration of a phorbol ester.

This finding can be applied to test other non-recombinant cell lines to attempt to upregulate expression of selected target proteins such as PDE4 isoenzymes.

The expression <<target protein >>, when used herein, is intended to designate a single protein or group of proteins possessing the same biological properties but bearing structural differences. For instance, a preferred target protein of the invention is the isoenzyme generally designated as PDE4A. In fact, PDE4A represents a family of proteins which all share the same catalytic domain but which differ in the sequence of their amino terminus.

In one of its preferred embodiments, the invention therefore comprises the method that was used to set up a particular PDE4A selective cellular assay. In this part of the invention we describe the characterization and quantification methods that were used to show differences in PDE4 subtype expression profiles in phorbol ester-treated cells compared to control cells. This comprises the comparison of the enzymatic activity pattern of phosphodiesterase in phorbol ester-treated cells and in control cells.

Thus, a particular embodiment of the invention concerns a method for the development of the PDE4A selective cellular assay for the screening of a candidate molecule that modulates the activity of the human phosphodiesterase 4A (PDE 4A). The method comprises the steps of:

a) incubating non-recombinant cells from the HL 60 cell line in the presence of a phorbol ester such as phorbol myristate acetate (PMA) without changing the culture medium during incubation, b) harvesting the cultured cells and preferably rinsing many times the residual PMA before further utilization, c) separating and counting the differentiated cells, preferably to use them either for the analysis of the PDE4 subtypes expression profile, or for determination of the PDE enzyme activity profiles.

Preferably, the phorbol ester is present in the culture medium at a concentration ranging from 0.1 to 3 $\mu$M, preferably from 0.5 to 1.5 $\mu$M; and most preferably, at a concentration of 1 $\mu$M. The incubation time of the cells in the medium containing the phorbol ester preferably ranges from 2 to 7 days, most preferably from 4 to 7 days. These concentrations and incubation times are not limited to the development of cell lines expressing a PDE4 subtype.

The PDE4 subtype transcripts found in PMA-treated HL-60 cells are preferably characterized, quantified and compared to control cells, through a method comprising the following steps:

a) incubating non-recombinant cells, preferably cells from a HL 60 cell line, in the presence of a concentration of a phorbol ester, preferably phorbol myristate acetate (PMA), which is sufficient to significantly upgrade PDE4 expression in the cell;

b) harvesting the cultured cells and extracting the total RNA;

c) incubating the total RNA extract with random polynucleotide hexamers in the presence of an enzyme having a reverse transcriptase activity to generate cDNA, d) amplifying the cDNA obtained in step c) with a pair of oligonucleotide primers that hybridize specifically to human PDE 4A cDNA;

f) detecting and quantifying the amplified nucleic acid.

In a preferred embodiment of the method described above, the detection and quantification of the PDE4 amplified nucleic acid comprises the steps of:

a) bringing into contact the amplified PDE4 nucleic acid with polynucleotide probes that hybridize specifically to the human PDE4 subtypes mRNA or to any nucleic acid strand of the human PDE4 subtypes cDNA;

b) detecting the nucleic acid hybrid complexes formed.

Preferably, the detection and quantification of amplified nucleic acid is performed with a polynucleotide probe, for example a probe that hybridizes specifically to human PDE 4A mRNA or to any nucleic acid strand of the human PDE 4A cDNA.

Some specific primers and probes that hybridize specifically with the PDE 4A mRNA or any strand of the human PDE 4A cDNA may be designed on the basis of the nucleic acid sequence of phosphodiesterase 4A that is disclosed in Livi et al. (1990) incorporate herein by reference.

The primers and probes used for performing the characterization method described above can be prepared by any suitable method, including for example, cloning and restriction of appropriate sequences and direct chemical synthesis by a method such as the phosphodiester method of Narang et al. (1979), the phosphodiester method of Brown et al. (1979), the diethylphosphoramidic method of Boccage et al. (1981) and the solid support method described in EP 0 707 592. The disclosures of all these documents are herein incorporated by reference.

The PCR technology is the preferred amplification technique used in the present invention. The variety of PCR techniques are familiar to those skilled in the art.

For a review of PCR technology, see White (1997) and the publication entitled "PCR methods and applications" (1991, Cold Spring Harbor Laboratory Press).

PCR primers on either side of the PDE 4A nucleic acid sequences to be amplified are added to a suitably prepared nucleic acid sample along with dNTPs and a thermostable polymerase such as Taq polymerase.

The nucleic acid in the sample is denatured and the PCR primers are specifically hybridized to complement a nucleic acid sequence in the sample. The hybridized primers are extended. Thereafter, another cycle of denaturation, hybridization, and extension is initiated.

The cycles are repeated several times to produce an amplified fragment containing the nucleic acid sequence between the primer sites.

An illustrative embodiment of a PCR method that can be used for performing the characterization of the invention is described herein in the examples.

Preferably, the primers used to perform the amplification reaction of the characterization study of the invention are selected from the group consisting of the nucleotide sequences of SEQ ID N°1 and SEQ ID N°2.

In this characterization study involving steps in which an expression analysis of the PDE 4A mRNA is performed, a quantity of PDE 4A mRNA or cDNA obtained from the control cells is compared to the quantity of PDE 4A mRNA or cDNA obtained from PMA-treated HL 60 cell cultures.

In a preferred embodiment of the characterization study described above, the detection and quantification of the PDE 4A amplified nucleic acid comprises the steps of:

a) bringing into contact the amplified PDE 4A nucleic acid with a polynucleotide probe that hybridizes specifically to the human PDE 4A mRNA or to any nucleic acids strand of the human PDE 4A cDNA;

b) detecting the nucleic acid hybrid complex formed.

Preferably, the detection probe is labelled.

In another embodiment of the characterization study described above, the amplified nucleic acid is labelled.

Any of the probes or primers of the present invention can be labelled if desired, by incorporating a label detectable by spectroscopic, photochemical, biochemical, immunochemical, or chemical means.

For example, useful labels include radioactive substances ($^{32}P$, 35S, $^3H$, 125I), fluorescent dyes (5-bromodesoxyuridin, fluorescein, acetylaminofluoren, digoxygenin) or biotin.

In a preferred embodiment, the detection probe used for performing the characterization study of the invention is labelled with biotin.

In another preferred embodiment of the characterization study of the invention, the amplified nucleic acid is labelled with digoxygenin.

A further preferred method to characterize the enzymatic activity of the human phosphodiesterases (PDE) found in PMA-treated HL-60 cells compared to control cells, comprises the steps of:

a) Extracting cytosolic protein content from the PMA-treated and control HL-60 cells in an appropriate lysis buffer;

b) applying the extracted proteins onto a FPLC column to separate the different phosphodiesterase activities;

c) collecting the separated FPLC fractions and preserving an aliquot from each one for PDE activity measurement;

d) measuring PDE activities extracted from PMA-treated and control HL-60 cells using a modification of the method described by Smith et al. (1993);

In the methods described above, the human phosphodiesterase activities are measured both in cultures of PMA-treated and in control HL-60 cells in order to compare the profile and the level of PDE activities in both cell lysates. The activity of human PDEs can be assessed by the capacity of the enzymes to hydrolyse several cyclic monophosphate nucleotides such as cAMP and cGMP; the level of cAMP hydrolysis is performed on the cytosolic fraction of the cell lysate.

The cytosolic fraction of the cell lysate may be obtained by lysing the PMA-treated HL60 cells harvested from the culture plates, for example by sonication, or by one or several cycles of freezing-thawing, then by extracting the proteins and centrifuging the cell pellets in order to collect the supernatant which contains the cytosolic enzymes, optionally after filtration of the supernatant through a 0.2 $\mu$m filter.

In another embodiment of this method, the quantification of the level of cAMP hydrolysis is performed on successive aliquot fractions from the chromatography eluate of the cytosolic fraction of the cell lysate.

Although it clearly appears from the examples of the present application that upregulation of specific protein expression may not be achieved for all non-recombinant cell lines, the inventors findings provide appropriate guidelines for the skilled person to carry out suitable testing on a wide variety of potential candidates. The protein whose expression is to be regulated can vary substantially and is not intended to be restricted to PDE4 isoenzymes, although recombinant cell lines with an upregulated PDE4 isoenzyme expression constitute preferred embodiments of the present invention.

In the preferred embodiment described above and in the examples, the inventors have found that cells from the human HL60 cell line mainly express the PDE 4A isoenzyme after treatement with phorbol myristate acetate.

PMA treated non-recombinant cells such as HL60 cells represent valuable targets for screening candidate molecules that modulate the expression or the activity of human PDE 4A. For instance, PMA treated HL60 cell cultures allow the skilled person to screen for molecules that regulate the synthesis of phosphodiesterase 4A and also of molecules that inhibit the activity of the PDE 4A isoenzyme.

The methods of the invention for the screening of candidate molecules represent an improvement as regards to prior art methods in that they use non-recombinant cell lines that are selective for a single PDE 4 isoenzyme. The term "selective for a single PDE4 isoenzyme" is intended to designate cell lines which produce significant levels of a single PDE4 isoenzyme while the production of other PDE4 isoenzymes is downregulated to the point that these enzymes become virtually unmeasurable in the cells.

Thus, a further object of the invention concerns a method for the screening of a candidate molecule that modulates the expression or the activity of human phosphodiesterase 4A (PDE 4A). The method comprises the steps of:

a) Incubating non-recombinant cells, preferably cells from a HL 60 cell line, in the presence of a concentration of a phorbol ester, preferably phorbol myristate acetate (PMA), which is sufficient to significantly upregulate PDE4 expression the said cells;

b) adding a candidate molecule to the culture medium in which the phorbol ester-treated cells are cultured;

c) harvesting and disrupting the cells; and d) quantifying the cyclic AMP content in the cell lysate.

In the screening method of the invention, the potency of a candidate molecule to inhibit the activity of human phosphodiesterase 4A is assessed by measuring cAMP content in cells stimulated by an adenylate cyclase activator.

In a preferred embodiment of the screening method described above, the inhibition of human phosphodiesterase 4A activity is measured in cultures of PMA-treated HL 60 cells in the presence or in the absence of the candidate molecule to be assayed. The cAMP content measured in both cell lysates are compared in order to determine the capacity of the candidate molecule to modulate, and more particularly inhibit, the activity of the human phosphodiesterase 4A.

More specifically, a method for the screening of a candidate molecule that modulate the activity of the human phosphodiesterase 4A (PDE 4A) can comprise the following detailed process steps:

a) incubating cells from a HL-60 cell line in the presence of phorbol myristate acetate (PMA);

b) adding a candidate molecule at different concentrations for a determined time to the culture medium wherein the PMA-treated HL-60 cells are cultured;

c) adding an adenylate cyclase activator to allow cAMP level to increase in the cells for a short time;

d) adding a stop solution to control the effect of the adenylate cyclase activator;

e) disrupting and lysing the cells to collect their supernatant for cAMP measurement;

f) measuring cAMP content in each cell population treated with different concentration of candidate molecule;

g) comparing the cAMP content in the PMA-treated HL-60 in the presence or absence of candidate molecule to test.

The inhibitory potency of the molecules is determined by the evaluation of the cAMP levels in the PMA-treated HL-60 cells when the molecule to test is added to the cell culture.

In a further embodiment of the screening method of the invention, the HL-60 cells are cultivated in 24-wells plate before and during PMA treatment; this allows the comparison of the effect of different concentrations of a candidate molecule on an homogenous cell population in the same culture plate.

In a further embodiment of the first screening method of the invention, the analysis of the cAMP contents is performed on the cytosolic fraction of the cell lysate.

The cytosolic fraction of a cell lysate can be obtained by lysing the PMA-treated HL60 cells harvested from the culture plates, for example by sonication, then by centrifuging the cell homogenate in order to discard the pellet (particulate fraction composed mainly by cell membranes and non-soluble entities) and to collect the supernatant. This supernatant contains the cytosolic and soluble components; preferentially the cyclic nucleotides.

More specifically, prior to disruption and lysis of the cells, the cell medium is preferably discarded and the cell culture washed with phosphate saline buffer (PBS). The cell lysate may be obtained by sonication or by manual scraping; then the lysate can be collected for direct cAMP measurement or optionally can be frozen for further determination.

In the screening method described above, the level of cAMP in PMA-treated HL-60 cells incubated in the presence or in the absence of the candidate molecule is measured by an Enzyme Immuno-Assay (EIA). The measurement of the protein content in each cells-containing well is also performed by spectrophotometric determination.

The present invention will be further illustrated, without being limited to, by the following examples.

EXAMPLES

A) Materials and Methods

1) Materials

RPMI-1640 medium, fetal calf serum, L-glutamine, gentamycin, PBS and HEPES were from Gibco/BRL. Salbutamol, PMA, dexamethazone, benzamidine hydrochloride, PMSF, SBTI, EDTA, bis-TRIS, DTT, bacitracine, BSA, TES, cAMP, ethidium bromide were from Sigma (St-Quentin-Fallavier, France). [$^3$H]cAMP and [$^{14}$C] AMP were from Amersham International. Rolipram was synthesized by the department of therapeutic chemistry in Jouveinal Institute of Research (Fresnes, France). First-strand cDNA synthesis kit, PCR-Dig labeling kit and PCR-ELISA Dig detection kit were from Boehringer-Mannheim.

2) Methods

Reverse Transcription and Semi-quantitative RT-PCR

RNA was purified using Tripure™ Isolation Reagent, a single-step liquid phase separation issued from the total RNA isolation method developed by Chomczynski and Sacchi (1987). Washed and pelleted cells were resuspended at a concentration of $1 \times 10^6$ cells/ml Tripure and the total RNA extracted was quantified spectrophotometrically RT-PCR was carried out using the commercial PCR ELISA Dig Labelling Kit. First strand cDNA was generated from 1 µg of total RNA per sample using random hexamers to prime the reverse transcription (First Strand cDNA Synthesis Kit for RT-PCR) and was directly amplified by PCR following the addition of specific primer pairs.

Oligonucleotide primers were: PDE4A, 5'-TCGGAGCTGGCGCTCATGTAC-3' is (SEQ ID N°1) and 5'-GGCAGTGTGCTTGTCACAGAT-3' (SEQ ID N°2), defining a 439-bp product; PDE4B, 5'-AGCTCATGACCCAGATAAGTG-3' and 5'-GCAGCGTGCAGGCTGTTGTGA-3', defining a 327-bp product; PDE4C, 5'-CGCTCAGATAGCGACTATGAA-3' and 5'-TCCGCTTGAACTTGTTGGAGG-3' defining a 331-bp product; PDE4D, 5'-GGCCTCCAACAAGTTTAAAA-3' and 5'-ACCAGACAACTCTGCTATTCT-3', defining a 339-bp product. The 5'-biotin-labelled capture probes used for the detection of PCR fragments were: 5'-AGCGCCAGCGCAGAGGCTAC-3' for PDE4A, 5'-TAGACCCCTAACATG-3' for PDE4B, 5'-AGCAGCCAAGCAGGGACCC-3' for PDE4C, 5'-CAATGTCTCAGATCAGTGGA-3' for PDE4D. Briefly, this PCR ELISA allows the specific detection of PCR products in a semi-quantitative microtiter plate format. The PCR products are labelled with digoxigenin during the amplification process (dig labelling). The labelled PCR products are analyzed by solution hybridization to a specific capture probe that is complementary to the inner part of the amplification product (dig detection). This capture probe is labelled with biotin to allow immobilization of the hybrid to a streptavidin coated microtiterplate surface. Unspecific amplification products will not hybridized to this capture probe and thus will be removed during the following washing steps; The bound hybrid is detected by an anti-digoxigenin peroxidase conjugate and by use of the colorimetric substrate ABTS. In comparison with suitable standards the color signal can be used for semi-quantitative evaluation of an amplification reaction. In our experiments the PDE4 subtypes PCR fragments amplified in the control cells (cells non treated with any of the compound tested), were our standards and the optical densities found for these PCR-fragments were normalized to 1.

Cell Culture

All the cell lines used in this study were obtained from the European Collection of Cell Culture (ECACC). U-937, HT-29, HL-60, Jurkat, MOLT-4, HK-293, CACO2 were grown in RPMI 1640 medium supplemented with 10% (v/v) heat-inactivated calf serum at 37° C. in an humidified atmosphere of 95% air-5% CO2. Culture media were changed every 2 to 3 days and always 24 hr before addition of the compounds tested: 1 $\mu$M PMA (72 hrs), 1 $\mu$M dexamethazone (2 hrs) or a combination of 1 $\mu$M salbutamol and 30 $\mu$M rolipram (2 hrs). Cells in suspension were seeded at $10^6$ cells/ml and adherent ones were used when confluent. After the required incubation times, $10^6$ cells were used for mRNA extraction and $2.5 \times 10^8$ for proteins extraction.

Protein Extraction and Chromatographic Resolution of PDE Activities

The adherent cells were disrupted by trypsinisation and along with the non-adherent cells were washed carefully at least twice with sterile PBS and counted. After 5 min centrifugation at 2000 rpm the cell pellets ($2.5 \times 10^8$ cells) were frozen and stored at $-85°$ C. prior to use. Cell pellets were resuspended in an extraction buffer ($10^8$ cells/4 ml): 20 mM bis-Tris buffer, pH 6.5, containing 2 mM EDTA, 2 mM DTT, 0.1 mM PMSF, 2 $\mu$g/ml SBTI, 100 $\mu$g:ml bacitracine and 2 mM benzamidine, and sonicated on ice. The homogenate was then centrifuged at 28000 g for 60 min at 4° C. After centrifugation the pellet was discarded and the supernatant frozen at $-80°$ C. if not used immediately. The supernatant which contained the cytosolic enzymes was filtered through a 0.2 $\mu$m filter and applied onto a FPLC column (MonoQ HR 5/5, Pharmacia). The elution was performed at a flow rate of 1 ml/min with a linear gradient of NaCl (0–0.6 M) in a 20 mM bis-Tris buffer, pH 6.5, containing 2 mM EDTA, 2 mM DTT, 0.1 M PMSF and 2 mM benzamidine. Fractions of 1.5 ml were collected and stabilized by addition of BSA (1 mg/ml). An aliquot of each fraction was taken for further phosphodiesterase activities determination and the rest was stored at $-85°$ C.

Phosphodiesterase Assay

Phosphodiesterase activities were assayed using a modification of the method described by Smith et al. (1993) utilizing the observation that 5'-nucleotides bind very strongly to alumina while the cyclic nucleotides are readily eluted at neutral or slightly alkaline pH. Assays were performed in 96-well plate at 37° C. in a total volume of 200 $\mu$l. Each well contained 5 $\mu$l of each eluted fractions and assay buffer (final concentration of 40 mM Tris-HCl, pH 8.0, 5 mM $MgCl_2$, 4 mM $\beta$-mercaptoethanol, 10 nM [$^3$H]cAMP and 10 $\mu$M cAMP); for the identification of the phosphodiesterase activities found, cGMP was also used to replace cAMP as a substrate and $Ca^{2+}$ (2 mM), calmodulin (4 units/well), cGMP (10 $\mu$M) and rolipram (30 $\mu$M) were used as modulators of activity. Following 60 min incubation, the reactions were terminated by the addition of [$^{14}$C]AMP (1 $\mu$M) in TFA (0.5%). Membrane-bottomed microtiter plates (Silent monitor, Nalge Nunc) filled with 50 mg alumina were equilibrated with 0.1M TES-NaOH, pH 8.0. The reaction mixtures were applied to these "alumina micro-columns" and the non-hydrolyzed cAMP was eluted with 3 ml equilibration buffer. The [$^3$H]AMP and [$^{14}$C]AMP were then eluted with 2 ml NaOH directly into scintillation vials containing alkali-compatible scintillant (Ultima gold, Packard). The separated [$^3$H]cAMP was back-corrected for recovery using the separated and non-separated $^{14}$C values and expressed as a fraction of the total [$^3$H]CAMP to give the amount of substrate hydrolyzed.

Cell Culture for the Screening of Candidate Molecules

HL-60 cells were seeded in 24-wells plate at a concentration of $1.5 \times 10^6$ cells/ml culture medium and 1 $\mu$M PMA, dissolved in DMSO was added in each well. The plate is incubated for 72 h at 37° C. in an humidified atmosphere of 95% air-5% $CO_2$. After the 72 h of differentiation period, the culture medium is removed by aspiration and each well is washed with PBS. The candidate molecules are added in the well diluted in 150 mM Tris/HCl buffer, 2 mM EDTA, pH 7.4 to reach the desired concentrations to test. The cells are then incubated for 30 min at 37° C. under gentle shaking before addition of 10 $\mu$M forskolin, adenylate cyclase activator, for 15 min. After the activation time, the plate is stored on ice and 200 $\mu$l of stop solution, composed by 0.2M HCl, 1% Triton X100, 0.2 mM IBMX, is added in each well. The cells are then disrupted by sonication to allow the measurement of intracellular cAMP produced during the reaction.

cAMP Measurement cAMP levels in each cell population treated with candidate molecule were evaluated using an EIA kit from Euromedex. This kit is a competitive immunoassay for the quantitative determination of cAMP in samples treated with 0.1 M HCl. The kit uses a cAMP polyclonal antibody to bind, in a competitive manner, the cAMP in the sample or an alkalin phosphatase molecule which has cAMP covalently attached to it. 280 $\mu$l of each sample are transferred to 96-wells plate to separate cellular cytosol from particulate fraction by centrifugation, 15 min at 3500 rpm, 4° C. The cytosolic fraction separated from the pellet is then transferred to a "transfer 96-wells plate", which is stored on ice until protein and cAMP measurement. 195 $\mu$l of each sample along with samples from the cAMP standard curve provided in the kit, are acetylated with 10 $\mu$l of a mix of 1:1/2 triethylamine:anhydrous acetic acid before competitive cAMP-EIA.

Example 1

Expression Profile of PDE4/mRNA Subtypes in the Cell Lines Tested

Cells were cultured and treated for 2 hours with a combination of 1 $\mu$M salbutamol/30 $\mu$M rolipram, 3 days with 1 $\mu$M PMA or 2 hours with 1 $\mu$M dexamethasone. The control cells received 1% DMSO for 2 hours or 3 days. After treated, the cells were washed and prepared for mRNA extraction as described in the Materials and Methods section. PCR fragments were quantified by semi-quantitative PCR: The expression of the subtypes in is control cells was normalized to 1 to allow expression of the data found in the treated cells as an x-fold increase or decrease expression of each subtype in comparison to the control value.

The expression profile of PDE4 subtypes was determined in each cell line using specific primers for RT-PCR. The cell lines used were chosen because the predominant and in some cases the only PDE activity present was PDE4. The results obtained are summarized in table 1 and showed that PDE4C was not found in any of the cell lines tested. In Molt and Jurkat cells we found a similar expression profile of the subtypes with a large predominance of PDE4A. The D subtype was slightly expressed and represents a mix of D1 and D2. D3 is not present in these cells. A very slight fragment corresponding to PDE4B seemed also to be present in Molt and Jurkat. In HL-60 cells, U-937 and HK-293 transcripts corresponding to the 3 subtypes A, B and D were found, with a large predominance of PDE4D (especially D3) in HK-293. In HT-29 PDE4D3 was predominant but 4D1/4D2 and 4A were also present with a trace of 4B transcript. In CACO-2 cells PDE4A and D (a mix D1, D2 and D3) were expressed.

In CACO-2 cells none of the treatment used affected the profile of PDE4 subtypes expression, except PMA that exhibited a slight up regulation (+1.5 fold) of total PDE4D expression.

TABLE 1

Expression of PDE4 subtypes in different human cell lines

|  | PDE 4A | PDE 4B | PDE 4C | PDE 4D1/D2 | PDE 4D3 |
|---|---|---|---|---|---|
| Molt-4 | ++ | − | − | + | − |
| Jurkat | ++ | +/− | − | + | − |
| HL-60 | + | ++ | − | +/− | + |
| U-937 | ++ | − | − | + | ++ |
| HK-293 | + | + | − | + | ++ |
| HT-29 | + | +/− | − | + | ++ |
| CACO-2 | ++ | − | − | + | + |

Example 2
Changes in Expression of PDE4 Subtypes During Treatment of the Different Cell Lines with PMA, Dexamethasone or Salbutamol/Rolipram Changes in PDE4 subtype expression were evaluated by semi-quantitative PCR after the treatment of the cells with salbutamol/rolipram, PMA and dexamethasone, and compared to control cells. The expression of the subtypes in control cells was normalized to 1 to be able to express the data found in the treated cells as an x-fold increase or decrease expression of each subtype in comparison to the control value. The results obtained are summarised in table 2 and here again, none of the treatment used was able to induce the expression of a C subtype.

In Molt-4 cells the expression level of PDE4 subtypes did not significantly change after the 2 hours incubation with salbutamol/rolipram. Expression of PDE4A was slightly down regulated under PMA (−1.5 fold) and up regulated (+2 fold) with dexamethasone; no change occurred for the other subtypes.

In Jurkat cells no regulation was observed under salbutamol/rolipram and dexamethasone treatments. In contrast, PMA led to the down regulation of PDE4B (−2 fold) and PDE4D (−1.9 fold) without affecting PDE4A levels.

In U-937 cells treated with salbutamol/rolipram, PDE4A was induced 3.2-fold and PDE4B 2-fold. PDE4D3 level was unaffected by this treatment in opposite to D1/D2 that were up regulated. Dexamethasone treatment was without effect on the subtype expression in this cell type.

Figure 1:
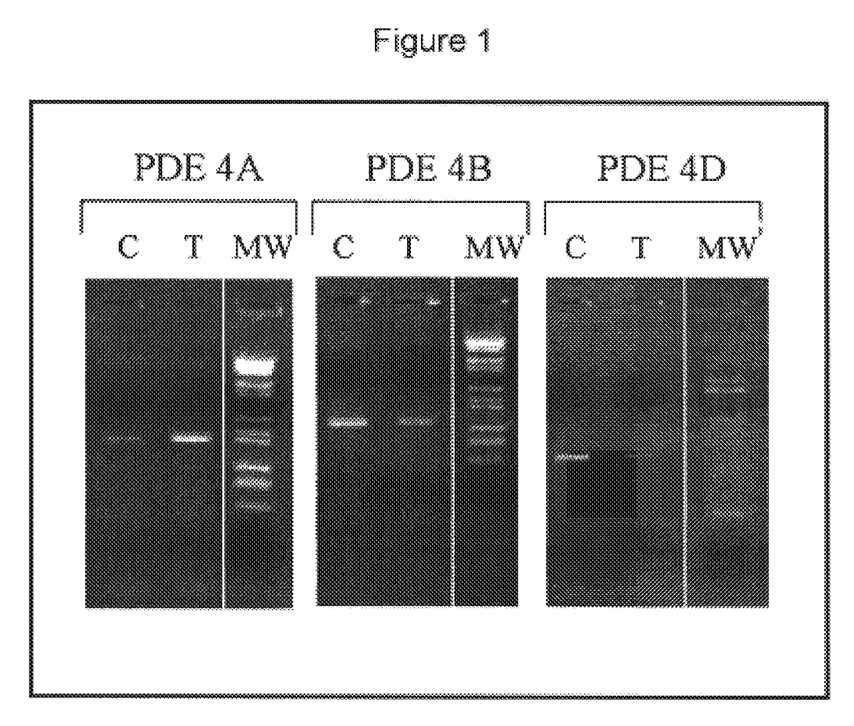
FIG. 1: Comparison of level of expression of PDE 4 subtypes in control cells and in PMA-treated HL60 cells One $\mu$g of total RNA from control cells (C) and PMA-treated HL-60 cells (T) was reverse transcribed and amplified with subtype specific PDE4 primers. The analysis of the PCR fragments was performed by electrophoresis on 1.5% agarose gels and visualized by ethidium bromide staining.

In HL-60 cells the increase of intracellular level of cAMP induced by salbutamol/rolipram up regulated the expression of PDE4A (+3.3 fold) along with PDE4D essentially through the variants D1 and D2. PDE4B level was unaffected by the raise in cAMP. Dexamethasone did not cause any change in the expression profile of the subtypes. The PMA effect was very interesting and led to an up regulation of PDE4A (+2.3 fold) and a down-regulation of the PDE4B and D signals that almost reached the negative control value. HL-60 cells treated with PMA were preferentially expressing the A subtype of the PDE4 enzymes (see FIG. 1).

In HT-29 PDE4D3 was still the predominant form of PDE4 subtypes but 4D1/4D2 and 4A were also present with a trace of 4B transcript. Neither salbutamol/rolipram nor dexamethasone were affected expression, but PMA up regulated the PDE4A and D expression.

PMA was a very potent up regulator of PDE4D expression in HK-293 cells (+3.7 fold) but did not affect any other subtype studied. In this cell line salbutamol/rolipram was also able to increase by a factor 2 the expression of PDE4B.

TABLE 2

Changes in the expression of PDE4 subtypes in human cell lines, following treatments with Salbutamol/rolipram, PMA or dexamethasone

| Cell lines | Treatment | A | B | D | D1/D2 | D3 |
|---|---|---|---|---|---|---|
| Molt-4 | Control | ++ (1) | +/− (1) | + (1) | + | − |
|  | Salb/Rol | ++ (1.3) | +/− (1) | + (1) | + | − |
|  | PMA | +/− (−1.5) | +/− (1) | + (1.1) | + | − |
|  | Dexa-methasone | +++ (2) | +/− (1) | + (1.1) | +/− | − |
| Jurkat | Control | ++ (1) | +/− (1) | + (1) | + | − |
|  | Salb/Rol | ++ (1.4) | +/− (1) | + (1.2) | + | − |
|  | PMA | ++ (1) | − (−2) | +/− (−1.9) | + | − |
|  | Dexa-methasone | ++ (1) | +/− (1) | + (1) | +/− | − |
| U-937 | Control | + (1) | ++ (1) | + (1) | + | ++ (1) |
|  | Salb/Rol | +++ (3.2) | +++ (2) | + (1) | ++ | ++ (1) |
|  | PMA |  |  |  |  |  |
|  | Dexa-methasone |  |  |  |  |  |
| HL-60 | Control | + (1) | ++ (1) | + (1) | +/− | + (1) |
|  | Salb/Rol | +++ (3.3) | ++ (1.3) | ++ (1.8) | + | +/− (−1.8) |
|  | PMA | ++ (2.3) | − (−12.2) | − (−14.5) | +/− | − |
|  | Dexa-methasone | + (1) | ++ (−1.2) | + (1) | + | + (1) |
| HK-293 | Control | + (1) | + (1) | ++ (1) | +++ | ++ (1) |
|  | Salb/Rol | + (1.1) | ++ (2.1) | ++ (1.4) | + | ++ (−1.1) |
|  | PMA | + (1) | +/− (1) | +++ (3.7) | + | ++ (1) |
|  | Dexa-methasone | + (1) | +/− (−1.5) | ++ (1) | + | ++ (1) |
| HT-29 | Control | + (1) | +/− (1) | + (1) | + | ++ (1) |
|  | Salb/Rol | + (1) | +/− (−1.2) | + (1.1) | + | ++ (1) |
|  | PMA | ++ (1.5) | − | ++ (1.8) | + | ++ (1) |
|  | Dexa-methasone | + (1) | − | + (1) | +/− | ++ (1) |
| CACO-2 | Control | ++ (1) | − | + (1) | + | + (1) |
|  | Salb/Rol | ++ (1) | − | + (−1.1) | + | + (1.2) |
|  | PMA | ++ (1) | − | ++ (1.5) | ++ | + (−1.1) |
|  | Dexa-methasone | ++ (1) | − | + (1) | + | + (1) |

Figure 2A:
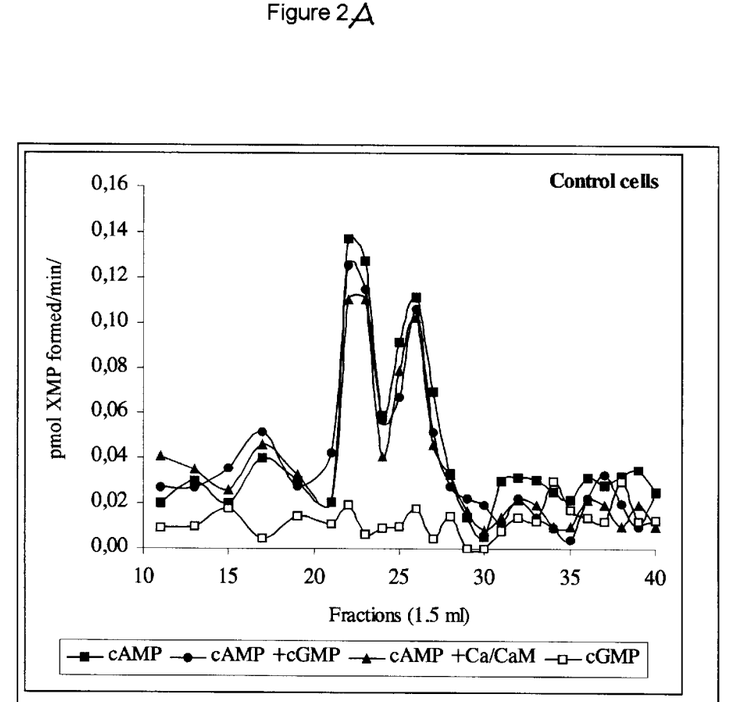
Figure 2B:
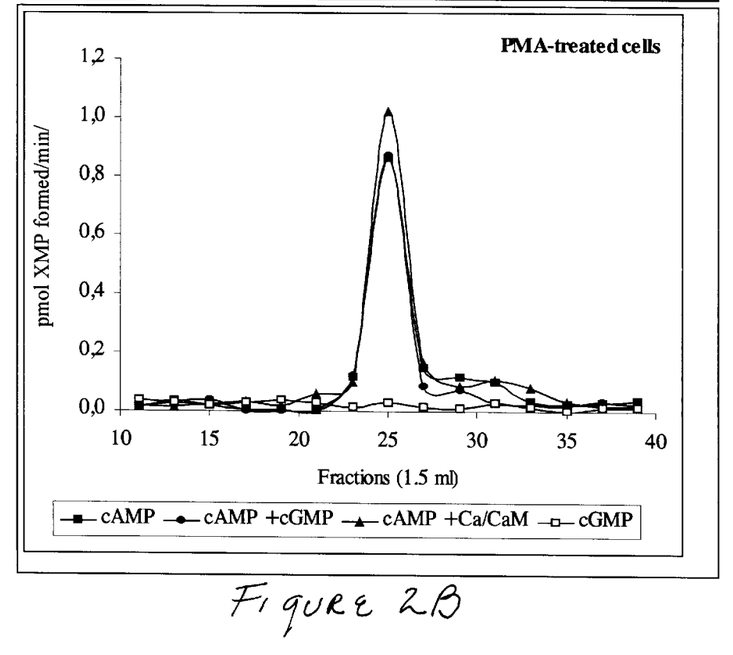
Figure 3A:
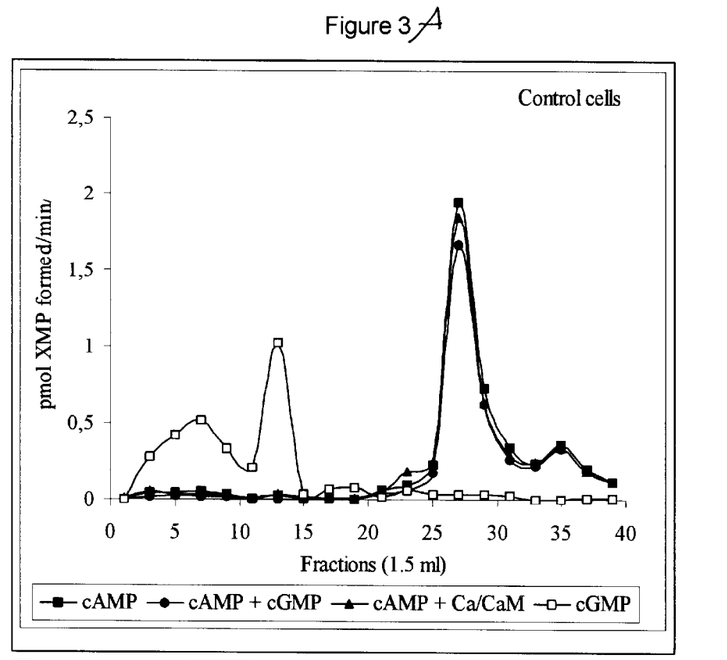
Figure 3B:
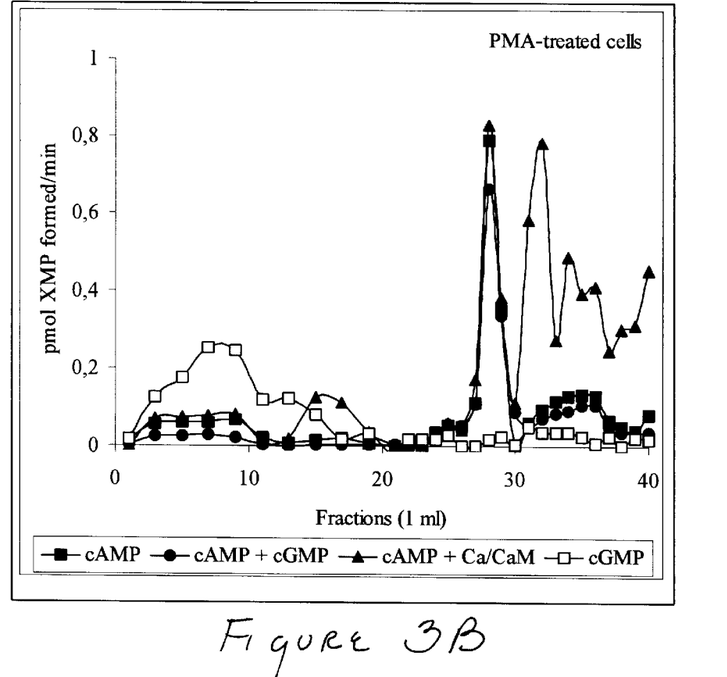

Example 3
Separation and Identification of PDE Activities Found in Control and Treated Cell Lines These studies were conducted originally to set up PDE4 subtype cellular assays, for this reason the cell lines that were expressing either a single or majority of a single subtype after the different treatments, were analysed for their phosphodiesterase activities. Among the entire cell lines tested only HL-60 and HK-293 fulfilled this criteria after a 3 day-incubation with PMA; HL60 was a potential PDE4A selective cell line while HK-293 was a potential PDE4D selective cell line. In HL-60 cells, PMA treatment for 72 hours induced a significant decrease of PDE4B and 4D transcription leading these cells to preferentially express PDE4A. A significant increase of the total PDE4 activity along with the disappearance of a cAMP-hydrolysing activity, probably due to PDE4B and D down regulation, was also seen in these cells; the maximum activity in control cells was 0.14 pmol AMP formed/min/µl compared to 0.9 pmol AMP formed/min/µl in PMA-treated cells. No other PDE activity occurred after the PMA treatment of HL-60 cells (FIG. 2). In HK-293 cells the same treatment induced an up-regulation of PDE4D transcription and the appearance of a PDE1 activity along with a down-regulation of PDE5 activity (FIG. 3). In PMA-treated HL-60 cells, we noticed a marked decrease of PDE4B and 4D expression and an up-regulation of PDE4A transcription. No other PDE activity was induced by the treatment.

Figure 4:
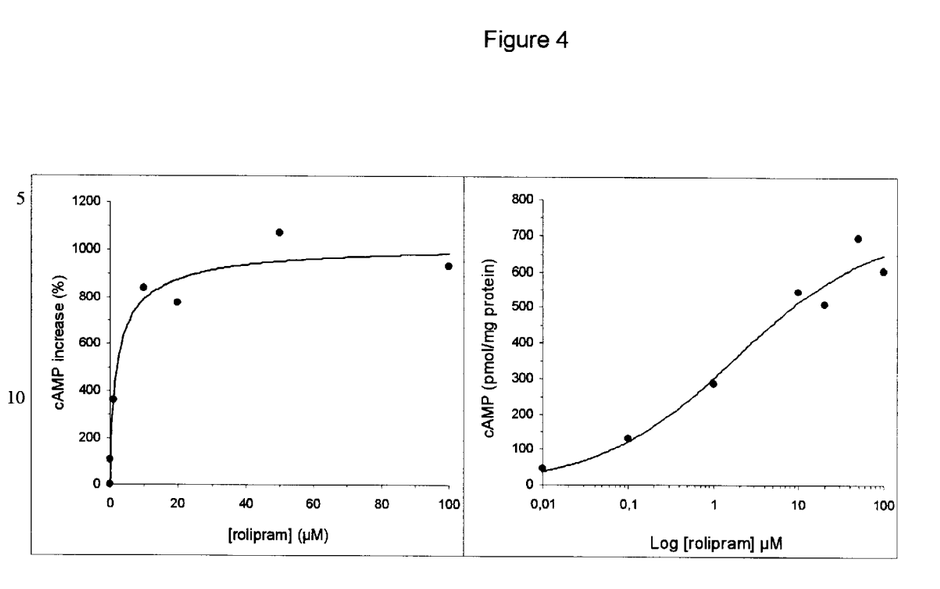
FIG. 4: Evaluation of the levels of cAMP in PMA-treated cells in the presence of different concentrations of a candidate PDE4 inhibitor to test.

Example 4
Utilization of the PMA-treated HL-60 Cells to Assess the Inhibitory Activity of a Candidate Molecule: Measurement of cAMP Increase in the Cells Incubated with Rolipram HL-60 cells were used in this experiment as a PDE 4A selective PDE4 subtype assay, to assess the inhibitory potency of rolipram, a well-known PDE4 inhibitor. As can be seen in FIG. 4 we obtained a classical dose-response curve; cAMP content increased when we increased the concentrations of rolipram used for PDE4A inhibition. We reached a plateau corresponding to a maximum cAMP release of 1038.9 pmol cAMP/mg total protein. the IC50 calculated for rolipram is 1.85 µM which is close to the in vitro values found in our experiments and in the litterature.

References

Beaucage et al., *Tetrahedron Lett* 1981, 22: 1859–1862
Brown E L, Belagaje R, Ryan M J, Khorana H G, 1979, *Methods Enzymol.*, 68:109–151
Chomczynski, P. and Sacchi N., 1987, *Anal. Biochem.*, 162: 156–159.
Livi, G. P.; Kmetz, P.; McHale, M. M., Cieslinski, L. B.; Sathe, G. M.; Taylor, D. P., Davis, R. L.; Torphy, T. J., Balcarek, 1990, *Molec. Cell. Biol.* 10: 2678–2686.
Narang S A, Hsiung H M, Brousseau R, 1979, *Methods Enzymol.*, 68:90–98
White, M. B. et al., 1997, *Genomics,* 12:301–306.
Smith et al., 1993, *Anal. Biochem.,* 241 355–357.

What is claimed is:

1. An assay for the screening of a candidate molecule that inhibits the expression or the activity of the human phosphodiesterase 4A (PDE 4A) comprising the steps of:
   a) incubating non-recombinant cells in the presence of a concentration of a phorbol ester sufficient to significantly increase PDE4 production in said cells;
   b) adding a candidate molecule to the culture medium in which the phorbol ester-treated cells are cultured;
   c) harvesting and disrupting the cells to produce a cell lysate;
   d) quantifying cyclic-3',5'-adenosine monophosphate (cAMP) content in the cell lysate; and
   e) comparing the cAMP content measured in step d) with the cAMP content in the cell lysate of the phorbol ester treated cells cultured in the absence of the candidate molecule.

2. The assay of claim 1, wherein the phorbol ester is present in the culture medium at a concentration ranging from 0.5 to 1.5 $\mu$M.

3. The assay of claim 1, wherein the phorbol ester is present in the culture medium at the concentration of 1 $\mu$M.

4. The assay of claim 1, wherein the quantification of cAMP content is performed on a cytosolic fraction of the cell lysate.

5. The assay of claim 1, wherein the non-recombinant cells are from a HL60 cell line.

6. The assay of claim 1, wherein the phorbol ester is phorbol myristate acetate (PMA).

* * * * *